United States Patent
Satoh et al.

(10) Patent No.: US 8,220,642 B2
(45) Date of Patent: Jul. 17, 2012

(54) POLYSULFONE-BASED BLOOD TREATMENT MEMBRANE AND METHOD OF PRODUCING THE SAME

(75) Inventors: Junya Satoh, Tokyo (JP); Takahiro Ichi, Tokyo (JP); Shunji Maniwa, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 0 days.

(21) Appl. No.: 12/601,543

(22) PCT Filed: May 26, 2008

(86) PCT No.: PCT/JP2008/059622
§ 371 (c)(1),
(2), (4) Date: Feb. 4, 2010

(87) PCT Pub. No.: WO2008/146775
PCT Pub. Date: Dec. 4, 2008

(65) Prior Publication Data
US 2010/0133170 A1   Jun. 3, 2010

(30) Foreign Application Priority Data

May 25, 2007 (JP) ................................. 2007-138554
Jul. 23, 2007 (JP) ................................. 2007-190662

(51) Int. Cl.
*B01D 69/00* (2006.01)
*B01D 69/02* (2006.01)
*B01D 67/00* (2006.01)

(52) U.S. Cl. ............................. 210/500.24; 210/500.41

(58) Field of Classification Search ............. 210/500.41, 210/500.24
See application file for complete search history.

(56) References Cited

U.S. PATENT DOCUMENTS 4,588,407 A    5/1986  Isono et al.

(Continued)

FOREIGN PATENT DOCUMENTS

EP    0749775    12/1996

(Continued)

OTHER PUBLICATIONS

International Search Report dated Jun. 17, 2008 that issued with respect to PCT/JP2008/059622.

(Continued)

*Primary Examiner* — Vickie Kim
*Assistant Examiner* — Peter Keyworth
(74) *Attorney, Agent, or Firm* — Greenblum & Bernstein, PLC (57) ABSTRACT

A polysulfone-based blood treatment membrane that exhibits excellent antioxidant properties, excellent long-term storage stability, and a practical strength, and ensures high productivity, a polysulfone-based blood treatment membrane that exhibits excellent antioxidant properties and long-term storage stability, rarely allows endotoxins to enter a treatment liquid, exhibits a practical strength, and ensures high productivity, and a method of producing the same. A polysulfone-based blood treatment membrane includes a polysulfone-based resin, a hydrophilic polymer, and a lipophilic antioxidant, the membrane containing the lipophilic antioxidant in an amount of 30 to 76 mg per gram of the membrane, and the total amount of the lipophilic antioxidant present on the surface of the membrane being 4 to 25 mg per gram of the membrane. Another polysulfone-based blood treatment membrane contains a lipophilic antioxidant in an amount of 30 to 76 mg per gram of the membrane, wherein the inner surface of the membrane has a TOF-SIMS normalized peak intensity of the lipophilic antioxidant of $1.8 \times 10^{-4}$ or more, and the outer surface of the membrane has a TOF-SIMS normalized peak intensity of the lipophilic antioxidant of $2.4 \times 10^{-4}$ or more. A method of producing a polysulfone-based blood treatment membrane that includes a polysulfone-based resin, a hydrophilic polymer, and a lipophilic antioxidant includes producing a membrane intermediate that contains the lipophilic antioxidant in an amount of 30 to 76 mg per gram of the membrane intermediate, and heating the membrane intermediate at 100 to 180.degree. C. for 0.1 to 360 minutes in a dry state.

4 Claims, 2 Drawing Sheets

U.S. PATENT DOCUMENTS

| | | | |
|---|---|---|---|
| 5,340,480 A * | 8/1994 | Kawata et al. | 210/500.23 |
| 6,001,288 A * | 12/1999 | Saruhashi et al. | 264/41 |
| 6,478,960 B1 * | 11/2002 | Saruhashi et al. | 210/500.23 |
| 2001/0004976 A1 | 6/2001 | Kozawa et al. | |

FOREIGN PATENT DOCUMENTS

| | | |
|---|---|---|
| JP | 59-064058 | 4/1984 |
| JP | 7-178166 | 7/1995 |
| JP | 9-066225 | 3/1997 |
| JP | 10-151196 | 6/1998 |
| JP | 10-244000 | 9/1998 |
| JP | 2000-254222 | 9/2000 |
| JP | 2000-296931 | 10/2000 |
| JP | 2006-198611 | 8/2006 |
| JP | 2006-296931 | 11/2006 |
| TW | 467750 | 12/2001 |

OTHER PUBLICATIONS

International Preliminary Report on Patentability, including the Written Opinion (in English) mailed Jan. 21, 2010 that issued with respect to PCT/JP2008/059622.

Taiwan Office action that issued with respect to patent family member Taiwanese Patent Application No. 10020714350, mail date is Aug. 15, 2011.

China Office action that issued with respect to patent family member Chinese Patent Application No. 200880016431.X, mail date is Nov. 24, 2011.

* cited by examiner

POLYSULFONE-BASED BLOOD TREATMENT MEMBRANE AND METHOD OF PRODUCING THE SAME

BACKGROUND ART

A hollow fiber blood treatment apparatus that utilizes a permselective membrane has been widely used for extracorporeal circulation, hemodialysis, supplying oxygen to blood during cardiotomy, plasma separation, or the like. A polysulfone-based blood treatment membrane has been widely used in the field of a blood treatment membrane such as a dialysis membrane, a gas exchange membrane, and blood component separation membrane. In recent years, the membrane has been not only served as a separation membrane, but also attempted to reduce oxidative stress that adversely affects a long-term dialysis patient. As an approach of the attempt, removal of peroxides that cause oxidative stress, or rejuvenating the antioxidant ability of a living body can be given. For example, Patent Documents 1 and 2 disclose a blood treatment membrane having excellent antioxidant properties, and the membrane is obtained by coating the surface of a previously formed membrane with vitamin E that exhibits various physiological actions such as in vivo antioxidant action, biological membrane stabilizing action, platelet aggregation suppressing action and the like.

However, since the blood treatment membrane is coated with vitamin E after assembling an artificial organ, the production process becomes complex so that productivity decreases. Moreover, since the membrane is coated with vitamin E only on the surface thereof, a sufficient effect to a substance that may permeate the membrane cannot be achieved. Therefore, it is desirable that a lipophilic antioxidant be provided over the entire membrane.

In order to improve the above problems, a method of producing a hollow fiber blood treatment membrane, comprising using a core liquid that contains vitamin E, or immersing the blood treatment membrane in a bath that contains vitamin E so that the vitamin E is present over the blood treatment membrane material entirely, and the resultant blood treatment membrane has been proposed (Patent Document 3). This method is effective for streamlining of the production process and enabling vitamin E to be provided over the membrane material entirely. However, vitamin E cannot be applied to the inside of the polymer skeleton that forms the membrane base material, and therefore elution of a low-molecular-weight substance that is undesirable for a human body and caused by oxidative decomposition of the polymer forming the membrane during long-term storage of the blood treatment membrane, or breakage of the blood treatment membrane due to a decrease in elongation of the membrane may not be prevented.

As another approach oxidative stress may also be thought to alleviate by preventing an oxidation reaction that occurs during dialysis. In particular, it is considered to be useful to prevent entry of endotoxins from a dialysate that are very toxic to a living body. Specifically, when endotoxins have entered into blood and a body, oxygen radicals are produced and released from phagocytes as part of biological defense mechanism.

It is effective to use a hydrophobic membrane that easily adsorbs endotoxins in order to solve this problem. However, a conventional hydrophobic membrane cannot be used due to the poor blood compatibility thereof. For example, a hollow fiber membrane that is produced by causing a hydrophilic polymer to adhere to only the inner surface of the hollow fiber membrane comprising a polymer alloy of a polysulfone and a polyarylate so that the inner surface exhibits antithrombogenicity while the highly hydrophobic outer surface adsorbs and removes endotoxins, has been disclosed (Patent Document 4). This hollow fiber membrane is effective for preventing entry of endotoxins from a dialysate since the polymer alloy has high hydrophobicity. However, since the hydrophobicities of the porous area and the outer surface are too high, air can be passed through to only a small extent, and this adversely affects diffusion permeability through the membrane. Moreover, the above hollow fiber membrane is ineffective for the cause of oxidative stress other than endotoxins. Furthermore, since a hydrophilic polymer that serves as a pore-forming agent during membrane formation by a wet process is not used, it is difficult to control the pore diameter. This makes it difficult to control permeability.

A method of producing a hollow fiber membrane formed of a polysulfone and a hydrophilic polymer that includes providing the outer surface of the membrane with hydrophobicity to increase endotoxin adsorption properties by reducing the content of the hydrophilic polymer in the entire membrane material, and applying vitamin E or the like that exhibits anti-thrombogenic properties on only the inner surface of the membrane to provide blood compatibility, has been disclosed (Patent Document 5). However, since the hydrophilic polymer is present on the outer surface of the membrane, a problem due to loss of adsorptivity easily occurs even if the endotoxin permeability can be temporarily decreased. Moreover, since the amount of hydrophilic polymer present on the outer surface of the membrane is small, air is insufficiently passed through. According to the finding of the present inventors, when producing a membrane so that the outer surface of the membrane has a low hydrophilic polymer concentration, the hydrophilic polymer concentration on the inner surface of the membrane inevitably decreases, and thus the anti-thrombogenic properties become really insufficient. Patent Document 5 discloses applying vitamin E on the inner surface of the membrane material to improve platelet adsorption properties as a more preferred embodiment. However, Patent Document 5 does not take account of the distribution of vitamin E providing in the membrane material and an improvement in endotoxin adsorption properties by utilizing the distribution of vitamin E in the membrane material.

A blood treatment membrane which vitamin E is provided in the entire membrane including in the inside of the membrane base material by adding vitamin E to a membrane-forming raw spinning solution, and a method of producing the same have been disclosed (Patent Document 3). According to this membrane, since vitamin E is present everywhere in the entire membrane material, a surface state differing from that of a conventional blended membrane made from polymers such as a polysulfone and a hydrophilic polymer can be obtained so that endotoxin adsorption properties may be expected to increase by controlling skillfully. According to the finding of the present inventors, however, when a large amount of vitamin E is included in order to provide the outer surface of the membrane with sufficient hydrophobicity, the mechanical strength of the blood treatment membrane decreases to an impractical level. On the other hand, when the content of vitamin E is reduced to a level so as to maintain the practical strength of the membrane, the outer surface of the membrane cannot be provided with sufficient hydrophobicity. This is considered to be because vitamin E is segregated at the microdomain interface of the base polymer so that the intermolecular interaction of the base polymer is adversely affected. A membrane which vitamin E is coated on the entire surface of the membrane as in Patent Document 1 can prevent a decrease in strength. However, when the membrane already structurally-formed is subjected to a post-treatment such as coating, a significant change in the surface state due to a decrease in pore size and surface deposition by the coated material may occur.

This makes it difficult to employ such a membrane.

As described above, when modifying a blood treatment membrane formed from a polysulfone-based resin as a base polymer with a lipophilic antioxidant, it is very difficult for the resulting membrane to provide excellent antioxidant properties and long-term storage stability, a capability of preventing invasion of endotoxins through the outer surface of the membrane, and practical strength. However, a blood treatment membrane produced using a polysulfone-based resin as a base polymer has been increasingly demanded. Therefore, a polysulfone-based blood treatment membrane that exhibits the above properties and has high productivity and a method of producing the same have been strongly desired.

Patent Document 1: JP-A-H07-178166
Patent Document 2: JP-A-2000-296931
Patent Document 3: JP-A-H09-66225
Patent Document 4: JP-A-H10-151196
Patent Document 6: JP-A-2000-254222

DISCLOSURE OF THE INVENTION

Problems to be Solved by the Invention

An object of the present invention is to provide a polysulfone-based blood treatment membrane that exhibits excellent antioxidant properties, long-term storage stability, and practical strength, and ensures high productivity, and a method of producing the same. Another object of the present invention is to provide a polysulfone-based blood treatment membrane that exhibits excellent antioxidant properties and long-term storage stability, a capability of preventing invasion of endotoxins through the outer surface of the membrane and practical strength, and ensures high productivity, and a method of producing the same.

Means for Solving the Problems

The present inventors conducted extensive studies in order to achieve the above objects. As a result, the inventors found that, when producing a blood treatment membrane using a membrane-forming raw spinning solution to which a lipophilic antioxidant is added, even though the blood treatment membrane includes the lipophilic antioxidant to such an extent that a decrease in strength does not occur, that is, the membrane is insufficient in antioxidant properties, sufficient amount of lipophilic antioxidant can be provided on the surface of the membrane by applying a specific heat history and migrating the lipophilic antioxidant in the drying step. The inventors found that the first object can be achieved by the resulting blood treatment membrane. This finding has led to the completion of the present invention.

On the other hand, with regard to the second object, as described above endotoxin adsorption properties may be impaired, or another problem may occur even when significantly changing the hydrophilic/hydrophobic distribution on the inner and outer surfaces of a hollow fiber membrane, or merely reducing the amount of hydrophilic polymer. Moreover, various problems occur when coating a membrane with a lipophilic antioxidant or blending a lipophilic antioxidant into a membrane-forming raw spinning solution. Therefore, it was considered that any distribution structures are insufficient to achieve the above object.

The present inventors conducted studies on an ideal distribution structure of a lipophilic antioxidant, and conceived that the hydrophobicity of the surface of a membrane can be increased without reducing the amount of hydrophilic polymer (i.e., it may be possible to provide the conflict properties of hydrophilicity and hydrophobicity on the single surface of the membrane), if it may be possible to sufficiently cover the surface (particularly the outer surface) of a polysulfone membrane with a highly hydrophobic lipophilic antioxidant as a oil film (hydrophobic layer), and upward thereof provide a hydrated hydrophilic polymer chain which is penetrated through the hydrophobic layer so as to cover the entire membrane. The inventors estimated that such a surface may be obtained by providing the lipophilic antioxidant so as to migrate from the inside of the polymer phase during coagulation in forming the membrane instead of coating already structurally-formed membrane made from the polysulfone and the hydrophilic polymer with the lipophilic antioxidant. This may produce a hollow fiber membrane that has a high clinical effect and implements simultaneously the two approaches that reduce oxidative stress.

The inventors found that in order to achieve such a blood treatment membrane while providing a practicable mechanical strength at the same time, when producing a blood treatment membrane by adding a lipophilic antioxidant to a membrane-forming raw spinning solution, even though the blood treatment membrane containing a lipophilic antioxidant to such an extent that a decrease in strength does not occur, that is, the membrane having insufficient antioxidant properties and capabilities of preventing entry of endotoxins through the outer surface of the membrane is used, the lipophilic antioxidant can be seep out from the membrane base material (migration) by applying a specific heat history in the drying step so that a sufficient amount of lipophilic antioxidant can be provided on the surface of the membrane. The inventors further found that the second object can be achieved by the resulting blood treatment membrane. These findings have led to the completion of the present invention.

Specifically, the present invention is as follows:

(1) A polysulfone-based blood treatment membrane that is a permselective membrane comprising a polysulfone-based resin, a hydrophilic polymer and a lipophilic antioxidant, in which the membrane contains the lipophilic antioxidant in an amount of 30 to 76 mg per gram of the membrane, and the total amount of the lipophilic antioxidant present on the surface of the membrane is 4 to 25 mg per gram of the membrane.

(2) The polysulfone-based blood treatment membrane according to (1), wherein the membrane has TOF-SIMS normalized peak intensities, that are an index indicating the concentration of the lipophilic antioxidant on the surface of the membrane, of $1.4 \times 10^{-4}$ or more for the inner surface of the membrane, and of $1.8 \times 10^{-4}$ or more for the outer surface of the membrane.

(3) The polysulfone-based blood treatment membrane according to (1) or (2), wherein the lipophilic antioxidant is a lipophilic vitamin.

(4) A method of producing a polysulfone-based blood treatment membrane that is a permselective membrane formed from a polysulfone-based resin, a hydrophilic polymer and a lipophilic antioxidant, comprising producing a membrane intermediate that contains the lipophilic antioxidant in an amount of 30 to 76 mg per gram of the membrane intermediate, and heating the membrane intermediate at 100 to 180° C. for 0.1 to 360 minutes in a dry state.

(5) The method according to (4), wherein the membrane intermediate is heat-treated at 140 to 180° C. for 0.1 to 1 minute in a dry state.

(6) The method according to (4) or (5), wherein the membrane intermediate is produced using a membrane-forming raw spinning solution that includes the polysulfone-based resin, the hydrophilic polymer, the lipophilic antioxidant and a solvent.

(7) The method according to any one of (4) to (6), wherein the membrane intermediate is a hollow fiber and the membrane intermediate is heat-treated after winding and bundling the membrane intermediate.

(8) The method according to any one of (4) to (6), wherein the membrane intermediate is a hollow fiber, and the membrane intermediate is wound and bundled after heating the membrane intermediate.

(9) The method according to any one of (4) to (8), wherein the lipophilic antioxidant is a lipophilic vitamin.

(10) A polysulfone-based permselective membrane comprising a polysulfone-based resin, a hydrophilic polymer and a lipophilic antioxidant, and produced using a membrane-forming raw spinning solution including the polysulfone-based resin, the hydrophilic polymer, the lipophilic antioxidant and a solvent, in which the membrane is produced by obtaining a membrane intermediate that contains the lipophilic antioxidant in an amount of 30 to 76 mg per gram of the membrane intermediate, and then heat-treating the membrane intermediate at 100 to 180° C. for 0.1 to 360 minutes in a dry state with a water content equal to or less than saturation water content, so that the membrane contains the lipophilic antioxidant in an amount of 30 to 76 mg per gram of the membrane, and the total amount of the lipophilic antioxidant present on the surface of the membrane is 4 to 25 mg per gram of the membrane.

Effects of the Invention

According to the present invention, a polysulfone-based blood treatment membrane that includes a lipophilic antioxidant and exhibits excellent antioxidant properties, excellent long-term storage stability, and a practical strength can be provided. It has been difficult for conventional polysulfone-based blood treatment membranes having a lipophilic antioxidant to satisfy these properties simultaneously. Furthermore, according to the present invention, a polysulfone-based blood treatment membrane that includes a lipophilic antioxidant and exhibits excellent antioxidant properties and excellent long-term storage stability, a capability of preventing entry of endotoxins through the outer surface of the membrane, and a practical strength (these properties have been hardly satisfied simultaneously in the past) can be provided. Since the polysulfone-based blood treatment membrane according to the present invention is obtained using the membrane-forming raw spinning solution including the lipophilic antioxidant, a post-treatment step such as coating process is unnecessary. Therefore, the polysulfone-based blood treatment membrane ensures excellent productivity.

BRIEF DESCRIPTION OF THE DRAWINGS

FIG. 1 schematically shows a state in which individual pores formed the porous body are connected to form a through-hole.

BEST MODE FOR CARRYING OUT THE INVENTION

The term "polysulfone-based resin (hereinafter, refer to as "PSf")" used in the present invention is a generic name for polymers having a sulfone bond. For example, a PSf that includes a repeating unit shown by any of the following formulas (1) to (3) may be preferably used, but particularly limited thereto, since such a PSf is widely marketed and is easily available.

(1)

(2)

(3)

(4)

wherein Φ represents an aromatic ring, and n represents the number of repeating units. A PSf having the above structure is commercially available as trade-names of "Udel" (manufactured by Solvay Advanced Polymers) and "Ultrason" (manufactured by BASF). Several types of products that differ in the degree of polymerization and the like are available. In the present invention, a polymer alloy produced by blending a polymer shown by the formula (4) with a polymer shown by the formula (2) is also included within the scope of the term "polysulfone-based resin".

As the hydrophilic polymer used in the present invention, polyvinylpyrrolidone (hereinafter, refer to as "PVP"), polyethylene glycol, polyglycol monoester, starch and a derivative thereof, and a water-soluble cellulose derivative such as carboxymethyl cellulose or cellulose acetate may be used. These hydrophilic polymers may be used in combination. It is preferable to use PVP or polyethylene glycol from the viewpoint of spinning stability and affinity with the PSf, with PVP being most preferable.

PVP is a water-soluble polymer produced by vinyl polymerization of N-vinylpyrrolidone. Several PVPs with different molecular weight are commercially available as trade-name of "Plasdone" (manufactured by ISP Chemicals Corp.) and "Kollidon" (manufactured by BASF).

The lipophilic antioxidant used in the present invention is not particularly limited insofar as the lipophilic antioxidant exhibits reducibility and can be dissolved in a solvent of a membrane-forming raw spinning solution described below. The lipophilic antioxidant is preferably lipophilic vitamins from the viewpoint of biological safety and sufficient application results. Examples of the lipophilic vitamin include vitamin A, vitamin D, vitamin E, vitamin K, ubiquinone, and the like. Among these, vitamin E is preferable. Examples of vitamin E include α-tocopherol, α-tocopherol acetate, α-tocopherol nicotinate, β-tocopherol, γ-tocopherol, δ-tocopherol, and the like. These lipophilic vitamins may be used either alone or in combination. For example, commercially available α-tocopherol is mixture of the above vitamin E. If a lipophilic antioxidant that exhibits excellent biological safety is discovered or synthesized in the future, regardless of natural product or artificial product, use of such a lipophilic antioxidant is also within the scope of the present invention.

The polysulfone-based blood treatment membrane according to the present invention and a method of producing the same are described below.

A method of producing a hollow fiber membrane comprises at least a step of extruding a membrane-forming raw spinning solution containing a polysulfone-based resin (PSf), a hydrophilic polymer, a lipophilic antioxidant and a solvent from a spinneret together with a hollow-making inner solution, a step of coagulating the extruded raw spinning solution, and a step of drying the coagulated hollow fiber membrane. Specifically, a commonly known dry-and-wet membrane-forming technology can be applied.

A PSf, a hydrophilic polymer and a lipophilic antioxidant are dissolved in a common solvent to prepare a membrane-forming raw spinning solution. When the hydrophilic polymer is PVP and the lipophilic antioxidant is α-tocopherol, the common solvent may include dimethylacetamide (DMAc), dimethyl sulfoxide (DMSO), N-methyl-2-pyrrolidone, dimethylformamide, sulfolane, dioxane, or a mixture of two or more of these solvents. An additive such as water may be added to the membrane-forming raw spinning solution in order to control the pore size.

The PSf concentration in the membrane-forming raw spinning solution is not limited particularly insofar as the concentration is within a range that a membrane can be produced and the obtained membrane has properties as a permeable membrane. The PSf concentration may be 5 to 35 wt %, and preferably 10 to 30 wt %. It is preferable for the polymer to have a low concentration in order to achieve high water permeability, and the concentration is preferably 10 to 25 wt %. The PVP concentration is adjusted so that the mixing ratio of PVP with respect to the PSf is 27 wt % or less, preferably 18 to 27 wt %, and more preferably 20 to 27 wt %. If the mixing ratio of PVP with respect to the PSf is more than 27 wt %, the amount eluted tends to increase. Meanwhile, if the mixing ratio of PVP with respect to the PSf is less than 18 wt %, the PVP concentration in the inner surface of the membrane decreases, and unpreferably, a symptom of leucopenia, that the concentration of leukocytes in blood of a patient rapidly decreases, may be observed. The resulting hollow fiber membrane has a PVP concentration of the inner surface of 20 to 50%, and preferably 30 to 45%, and a PVP concentration of the outer surface of 30 to 70%, and preferably 40 to 65%. Therefore, the hollow fiber membrane exhibits excellent anti-thrombogenic properties and biocompatibility, and allows only a small amount of proteins, platelets, and the like to adhere to the surface of the hollow fiber membrane. The membrane has a stable water-removing capability, and exhibits an excellent effect in order to stably perform a treatment such as hemodialysis or hemofiltration.

The reason that a stable water-removing capability is obtained by adjusting the PVP concentration on the surface of the membrane to 20% or more is unclear. However, it is considered that the PVP concentration necessary for PVP of hydrophilic polymer to cover over the surface of polysulfone that is hydrophobic and easily adsorbs proteins and the like is 20% or more. Since the surface of the membrane is thus sufficiently hydrophilized, adsorption of proteins and the like onto the surface of the membrane is reduced so that a stable water-removing capability may be obtained. If the PVP concentration on the surface of the membrane is more than 50%, the surface of the membrane is further hydrophilized so that a more stable performance is obtained. On the other hand, risk that PVP may be eluted into blood during hemodialysis or the like may be accompanied, and a potential safety hazard may arise. Therefore, the PVP concentration is preferably 50% or less.

Note that the term "PVP concentration on the surface of the membrane" used here refers to the PVP concentration in the extremely thin surface layer of the membrane where blood comes in contact with the membrane. The PVP concentration on the surface of the membrane may be calculated from a value measured by X-ray photoelectron spectroscopy (hereinafter refer to as XPS) as described in detail in the examples below.

The concentration of the lipophilic antioxidant in the membrane-forming raw spinning solution must be appropriately adjusted so that the content of the lipophilic antioxidant in the resulting blood treatment membrane is within a predetermined range. The content of the lipophilic antioxidant must be 22 mg or more per gram of the membrane as described below, and preferably 30 mg or more, in order to provide sufficient antioxidant properties and prevent entry of endotoxins through the outer surface of the membrane. Since the mechanical strength of the membrane significantly decreases when excessive amounts of the lipophilic antioxidant exist, the content of the lipophilic antioxidant must be 76 mg or less.

Next, using a tube-in-orifice-type spinneret, a membrane-forming raw spinning solution and a hollow-making inner solution for coagulating the membrane-forming raw spinning solution are simultaneously extruded respectively from the orifice and the tube of the spinneret. Water or a coagulating solution of which the main component is water may be used as the hollow-making inner solution. In general, a mixed solution of the solvent used for the membrane-forming raw spinning solution and water is preferably used. For example, an aqueous solution of 0 to 60 wt % DMAc is used. The membrane-forming raw spinning solution extruded from the spinneret together with the hollow-making inner solution runs through air gap, is introduced into a coagulation bath containing water as a main component installed below the spinneret, and dipped in the coagulation bath to complete coagulation.

The resulting membrane structure has a dense skin layer on the inner surface of the hollow fiber, and has a porous structure between the skin layer and the outer surface. It is preferable for the membrane to have a porous structure in the viewpoint of increasing the effective area for adsorption when removal of endotoxins that enter through the outer surface. Then after washing with water or the like, a hollow fiber membrane intermediate may be obtained. The membrane intermediate is further dried by introducing into a dryer to obtain a hollow fiber membrane. It is also possible to dry the membrane intermediate after cutting and bundling in a wet state. Alternatively the membrane intermediate may be dried in a state of continuous running. In this case, crimping the hollow fiber membrane is preferable for the membrane to efficiently exhibit diffusion performance when used for hemodialysis.

The antioxidant properties and the capability of preventing entry of endotoxins through the outer surface of the membrane increase as the content of the lipophilic antioxidant in the blood treatment membrane increases. On the other hand, the mechanical strength of the membrane gradually decreases as the content of the lipophilic antioxidant in the blood treatment membrane increases. The mechanical strength of the membrane rapidly decreases when the content has exceeded a certain value. The reason is necessarily not clear. A decrease in mechanical strength mainly occurs due to a decrease in breaking elongation. Therefore, the following assumption may be considered from the above that the lipophilic antioxidant (e.g., vitamin E) is segregated at the microdomain interface of the membrane base polymer so that the interfacial adhesion ability gradually decreases, but almost the entire interface is occupied with the lipophilic antioxidant when the content of the lipophilic antioxidant has exceeded a certain value so that the interfacial adhesion is rapidly lost.

A blood treatment membrane is generally placed in a container and used often in the form of a module. However, if the mechanical strength of the membrane is insufficient, the membrane may break when producing a module or during handling. The mechanical strength may be indicated by toughness determined by a tensile test. When the blood treatment membrane is a hollow fiber membrane, it is sufficient practically if each hollow fiber membrane has a toughness of 1000 gf·%. The term "toughness" used herein refers to a value obtained by multiplying the breaking strength (gf) by the breaking elongation (%). A toughness measuring method is described in detail in the examples with regard to an analytical method.

As a result of extensive studies, the present inventors found that a toughness of more than 1000 gf·% is achieved when the content of the lipophilic antioxidant is 76 mg or less per gram of the blood treatment membrane in the case of the membrane produced using a polysulfone-based resin as the base polymer. Therefore, the content of the lipophilic antioxidant per gram of the blood treatment membrane must be 76 mg or less.

When using the blood treatment membrane according to the present invention, an area that comes in contact with a treatment target liquid, that is, only the lipophilic antioxidant present on the surface of the membrane, exhibits antioxidant properties, and the lipophilic antioxidant that is buried in the membrane base material and does not come in contact with the treatment target liquid is not directly involved in the antioxidant effect on the blood component. The term "surface of the membrane" used here refers to not only the inner surface of the hollow fiber membrane that directly comes in contact with blood, but also the outer surface of the hollow fiber membrane and the surface of the porous area of the membrane thickness portion. Blood corpuscles among the blood components come in contact with only the inner surface of the membrane, but liquid components such as proteins and peroxides such as active oxygen traverse to and from the membrane thickness portion by diffusion. Therefore, all of the surfaces of the membrane including the porous area and the outer surface contribute to the antioxidant effect. Accordingly, the antioxidant capability is affected by the total amount of the lipophilic antioxidant present on all of the surfaces of the membrane.

The amount of the lipophilic antioxidant present on the surface of the membrane may be evaluated by causing the membrane to come in contact with a metal salt aqueous solution, and determining the amount of reduced metal ions, or extracting only the lipophilic antioxidant present on the surface of the membrane with water containing a surfactant, and determining the amount of the lipophilic antioxidant using liquid chromatography, for example. The determination method utilizing a reaction with an iron(III) chloride aqueous solution is considered to detect the lipophilic antioxidant present on the surface of the membrane appropriately. In the present invention, the amount of the lipophilic antioxidant is determined by this method. The measuring method is described in detail in the examples. In the extraction method that is a well-known method utilizing an alcohol aqueous solution, if the alcohol concentration is high, the membrane base material is swollen, and the lipophilic antioxidant buried in the membrane base material is also extracted. On the other hand, the lipophilic antioxidant cannot be dissolved in the extraction liquid if the alcohol concentration is low. Therefore, this method is not suitable for evaluation of the blood treatment membrane according to the present invention.

The present inventors conducted experiments in which fresh human blood was caused to come in contact with the permselective membrane, and found that it is necessary that the lipophilic antioxidant be present on the surface of the membrane in an amount of 4 mg or more per gram of the membrane so that the permselective membrane according to the present invention exhibits an excellent antioxidant effect as compared with a conventional permselective membrane. "The membrane according to present invention exhibits an excellent antioxidant effect" means that the permselective membrane according to the present invention exhibits an excellent antioxidant effect as compared with a conventional permselective membrane (i.e., a membrane that does not include the lipophilic antioxidant) with a significant difference (risk factor: 5%) in an antioxidant capability test (n=3) in which fresh human blood is caused to come in contact with the membrane. The antioxidant capability test used in the present invention is described in detail in the examples below with regard to the analytical method.

A concrete target level with regard to the antioxidant properties of the membrane is still unclear, and the antioxidant capability is now discussed by means of relative comparison. However, when the blood of a patient repeatedly comes in contact with the membrane over several to several tens of years three times a week (4 to 5 hours) (e.g., hemodialysis therapy), the higher antioxidant properties, there is no doubt that in the antioxidant property the higher the better. Specifically, even though the antioxidant properties of the membrane are improved to only a small extent, it is fully expected that the patient will remarkably benefit from the antioxidant effect of the membrane after therapy over a long time. Therefore, a statistically significant difference from a conventional membrane as recognized above is very meaningful to evaluate an improvement in the antioxidant properties of the membrane.

The amount of the lipophilic antioxidant present on the surface of the membrane may be determined using the normalized peak intensity of the parent mass peak measured by TOF-SIMS (time-of-flight secondary ion mass spectrometry) as an index. The measuring method is described in detail in the examples below. The measurement depth of this method is very shallow (several to several tens of angstroms), therefore, it can be considered that only the lipophilic antioxidant that is exposed on the surface is detected. The inner surface and the outer surface of the membrane can be independently measured by this method, but, it is difficult to measure the amount of the lipophilic antioxidant in the porous area. However, the measured value of at least the porous area near the inner surface may be considered to be almost equivalent to that of the inner surface. Therefore, the measured value of the inner surface may be represented by the measured value of the porous area.

The present inventors conducted experiments in which fresh human blood was caused to come in contact with the blood treatment membrane, and found that it is preferable that the measured value of the normalized peak intensity be $1.8 \times 10^{-4}$ or more so that the blood treatment membrane according to the present invention exhibits an excellent antioxidant effect as compared with a conventional blood treatment membrane. The antioxidant capability test used in the present invention is described in detail in the examples below with regard to the analytical method.

In the blood treatment membrane according to the present invention, at least a certain amount of the lipophilic antioxidant must be present on the outer surface of the membrane and in the porous area of the membrane so that the blood treatment membrane exhibits a capability of preventing entry of endotoxins through the outer surface of the membrane during use. The amount of the lipophilic antioxidant present on the outer surface of the membrane can also be determined using the normalized peak intensity measured by TOF-SIMS as an index. The outer surface of the membrane and the surface of the porous area of the membrane prevent entry of endotoxins through the outer surface of the membrane. It is difficult to measure the amount of the lipophilic antioxidant present in the porous area, but, the measured value of at least the porous area near the outer surface may be considered to be almost equivalent to that of the outer surface. Specifically, a parameter necessary for providing a capability of preventing entry of endotoxins through the outer surface of the membrane can be represented by the normalized peak intensity of the outer surface of the membrane. The normalized peak intensity is preferably $2.4 \times 10^{-4}$ or more in order to achieve the desired function.

On the other hand, if an excessive lipophilic antioxidant is present on the surface of the membrane, the surface of the membrane is hydrophobized excessively, and it is undesirable in the viewpoint of removal of air mixed, or blood compatibility. However, since the content of the lipophilic antioxidant in the blood treatment membrane according to the present invention is limited to 30 to 76 mg per gram of the membrane, undesirable hydrophobization does not occur insofar as the heating conditions are within the range as described below. For example, when heating the membrane that includes the lipophilic antioxidant in an amount of 76 mg per gram of the membrane at 180° C. for one minute in a dry state, the normalized peak intensity of the lipophilic antioxidant on the outer surface of the resulting membrane is $1.0 \times 10^{-2}$. If within said range, undesirable hydrophobization does not occur.

As above, it is necessary for the blood treatment membrane according to the present invention to contain the lipophilic antioxidant in an amount of 30 to 76 mg per gram of the membrane. The amount of the lipophilic antioxidant on the surface of the membrane must be 4 mg or more per gram of the membrane. When separately measuring the inner surface and outer surface of the membrane, the inner surface of the membrane preferably has a normalized peak intensity of the lipophilic antioxidant of $1.8 \times 10^{-4}$ or more, and the outer surface of the membrane preferably has a normalized peak intensity of the lipophilic antioxidant of $2.4 \times 10^{-4}$ or more.

In the present invention, since the lipophilic antioxidant and PVP are present in the entire material and on the surface of the blood treatment membrane within the above ranges, the characteristic features of the hydrophilic surface, such as excellent air removal and blood compatibility, and the characteristic features of the hydrophobic surface, such as adsorption and removal of endotoxins, which inherently conflict each other, can be achieved together. Though the reason is unclear, it is considered that the hydrophobic layer of the lipophilic antioxidant covers the surface of the polysulfone membrane as an oil film and the hydrated hydrophilic polymer chain then covers the entire membrane so that the membrane surface alone provides the contradictory properties of hydrophilicity and hydrophobicity. A blood treatment membrane disclosed in Patent Documents 1, 3 and 4 that is obtained by coating the surface of the membrane with the lipophilic antioxidant cannot have the distribution structure according to the present invention. Because, since PVP can be dissolved in an organic solvent (e.g., ethanol) for the lipophilic antioxidant in spite of hydrophilicity, PVP has compatibility with the lipophilic antioxidant in the coating solvent so that part or most of the PVP is buried in the coated layer of the lipophilic antioxidant.

The above surface properties may be confirmed by the receding contact angle and the advancing contact angle of the outer surface measured using a dynamic contact angle measuring device while closing the ends of the blood treatment membrane. The measuring method is described in the examples below. Note that the receding contact angle indicates the contact angle in water (hydrophilic atmosphere), and the advancing contact angle indicates the contact angle in air (hydrophobic atmosphere). It is known that when a hydrophilic polymer chain having high mobility (e.g., polyethylene glycol) is present on a hydrophobic surface (e.g., polyurethane), the hydrophilic polymer chain becomes predominant in a hydrophilic atmosphere, and the hydrophobic surface becomes predominant in a hydrophobic atmosphere so that the relationship "receding contact angle<advancing contact angle" is satisfied (A. Takahara, N. J. Jo, T. Kajima, J. Biometer. Sci. Polymer Edn, Vol. 1, No. 1, pp. 17-29 (1989)).

A conventional polysulfone-based blood treatment membrane formed only of a PSf and PVP is also a combination of PSf of a hydrophobic surface and PVP of a hydrophilic polymer chain having high mobility. According to experiments conducted by the present inventors, the relationship "receding contact angle<advancing contact angle" was observed. There is no difference in receding contact angle between the blood treatment membrane according to the present invention and a conventional polysulfone-based blood treatment membrane formed of only PSf and PVP. This means that the outer surface of the blood treatment membrane according to the present invention has properties similar to those of the conventional PSf-PVP blood treatment membrane in a hydrophilic atmosphere. Specifically, the blood treatment membrane according to the present invention exhibits surface hydrophilicity in the same manner as the conventional PSf-PVP blood treatment membrane, that is, a sufficient amount of PVP that can be exposed on the surface is present on the outer surface of the membrane so that the properties of the PVP chain is considered to become predominant on the membrane surface in a hydrophilic atmosphere. As the result, it is considered that the blood treatment membrane according to the present invention exhibits excellent air removal during priming to the extent equal to the conventional PSf-PVP membrane, differing from the blood treatment membrane disclosed in Patent Documents 2 and 3.

On the other hand, the advancing contact angle of the blood treatment membrane according to the present invention is higher than that of the conventional polysulfone-based blood treatment membrane formed of only PSf and PVP. This means that the outer surface of the blood treatment membrane according to the present invention is more hydrophobic as compared with the conventional PSf-PVP blood treatment membrane in a hydrophobic atmosphere. Specifically, the hydrophobic surface of the blood treatment membrane according to the present invention may tend to become predominant instead of PVP in a hydrophobic atmosphere even though the membrane of the present invention can be exposed PVP in the amount equal to the conventional PSf-PVP blood treatment membrane on the outer surface thereof. As a result, since the hydrophobic surface of a macromolecule such as an endotoxin approaches the outer surface of the membrane even in water so that hydrophobicity becomes predominant, hydrophobicity further increases as compared with a conventional PSf surface so that the endotoxin adsorption capability is considered to further increase. It is considered that such a special structure is not formed by coating, but is formed by efficiently migrating the hydrophobic lipophilic antioxidant previously contained in the membrane-forming raw spinning solution to the outer surface of the membrane after a heat treatment described below.

The membrane structure of the blood treatment membrane according to the present invention and the mechanism of its effects are more conceptually described below based on the above finding relating to the dynamic contact angle. Specifically, as described in Patent Documents 2 and 3, when a hydrophobic surface is formed from the polymer itself by reducing or eliminating a hydrophilic polymer on the outer surface of the membrane, the hydrophobic surface is hard so that endotoxins come in contact with the hydrophobic surface at several points, and are bonded to the hydrophobic surface as if the endotoxins land on the hydrophobic surface. On the other hand, when a hydrophobic surface is formed by a low-molecular-weight lipophilic antioxidant, the hydrophobic surface is considered to be a soft oil membrane (oil layer). Therefore, endotoxins are embedded in the oil membrane (oil layer) in the same manner as in the cell membrane (lipid bilayer membrane) of a gram negative bacterium. As a result, it is considered that endotoxins are more steadily and firmly bonded to the outer surface of the blood treatment membrane according to the present invention, and the blood treatment membrane thus exhibits a high endotoxin retention capability.

A treatment condition that is important for obtaining the above membrane structure is described below.

Figure 1:
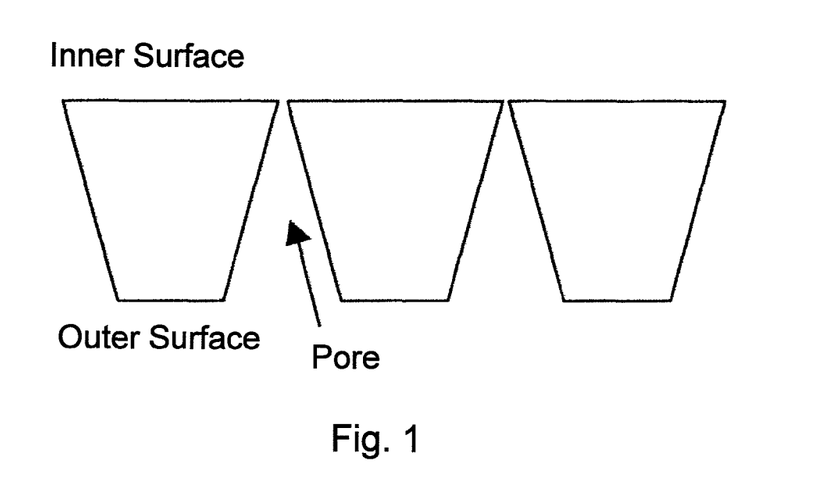
FIG. 1 is a schematic drawing showing a general polysulfone-based hollow treatment membrane, and corresponds to Comparative Example 1. The upper side of FIG. 1 corresponds to the inner surface of the hollow fiber, and the lower side of FIG. 1 corresponds to the outer surface of the hollow fiber. In the membrane shown in FIG. 1, a linear hole through which a liquid or eluate passes is formed through the membrane.

The present inventors conducted extensive studies so as to provide the polysulfone-based blood treatment membrane with excellent antioxidant properties and a practical strength. As a result, the inventors found that only the amount of the lipophilic antioxidant present on the surface of the membrane can be increased by heat-treating even the polysulfone-based blood treatment membrane that contains a lipophilic antioxidant in a specific dry state without changing the content of the lipophilic antioxidant in the entire membrane (i.e., while reliably maintaining a practical strength). This finding is described in detail below using schematic drawings. FIG. 1 is a schematic drawing showing a general polysulphone-based hollow treatment membrane. The upper side of FIG. 1 corresponds to the inner surface of the hollow fiber, and the lower side of FIG. 1 corresponds to the outer surface of the hollow fiber. In the membrane shown in FIG. 1, a linear hole through which a liquid or eluate passes is formed through the membrane. FIG. 1 schematically shows a state in which individual pores formed the porous body are connected to form a through-hole.

Figure 2:
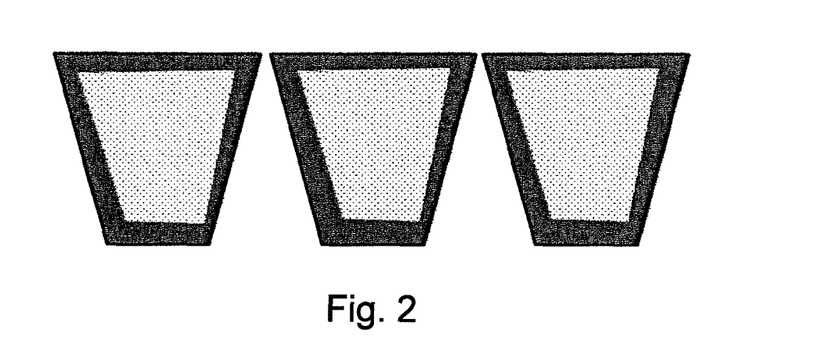
FIG. 2 is a schematic drawing showing a polysulfone-based hollow treatment membrane according to the present invention, and corresponds to the examples. The structure as the permeable membrane is the same as that of Comparative Example 1. Dots drawn on the membrane base material indicate a lipophilic antioxidant. The lipophilic antioxidant is not uniformly distributed in the membrane base material. Specifically, the concentration of the lipophilic antioxidant is high on the surface of the membrane (inner surface, pore surface, and outer surface). This phenomenon is referred to as "unevenly distribute on the surface of the membrane".
Figure 3:
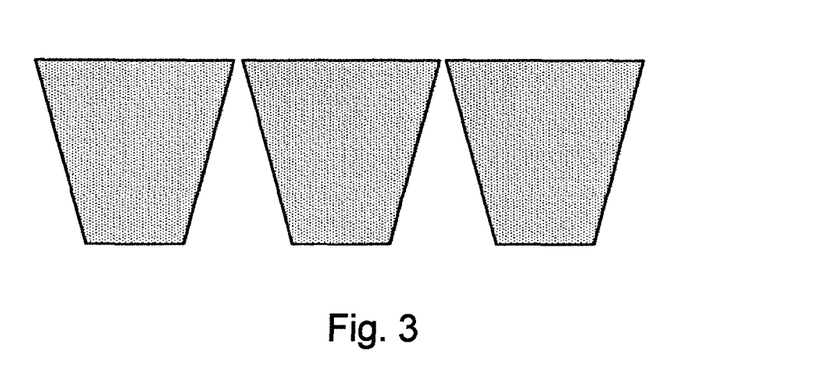
FIG. 3 is a schematic drawing showing polysulfone-based hollow treatment membranes of Comparative Examples 2, 4, 6, and 7. The lipophilic antioxidant is uniformly distributed in the membrane base material.

FIG. 3 shows a membrane formed by a production method using prior art. When forming a membrane using a membrane-forming raw spinning solution added with a lipophilic antioxidant according to the production method disclosed in Patent Document 3, the lipophilic antioxidant is uniformly distributed in the entire membrane as shown in FIG. 3. In FIG. 3, the distribution of the lipophilic antioxidant is indicated by dots. The blood treatment membrane according to the present invention is obtained by subjecting the membrane shown in FIG. 3 to a specific heat treatment. As a result of the heat treatment, the lipophilic antioxidant embedded in the polymer skeleton that forms the membrane base material migrates to the surface of the membrane so that the concentration of the lipophilic antioxidant on the surface of the membrane significantly increases as shown in FIG. 2. Specifically, a membrane structure in which the lipophilic antioxidant is unevenly distributed on the surface is formed. It is considered that this phenomenon occurs, since the lipophilic antioxidant is forced to move to the outside of the system as a result of activation of the molecular motion of the PS polymer chain by heating and the subsequent aggregation of the PS polymer chains. In a membrane mainly formed of a hydrophobic resin, a hydrophilic component such as glycerol or PVP is well-known to migrate with the movement of water during drying. However, it is surprising that the lipophilic antioxidant having high affinity to a hydrophobic resin migrates. Furthermore, it has been considered that when heating the lipophilic antioxidant in air, the lipophilic antioxidant is normally oxidized to lose antioxidant properties. Oxidation and inactivation are considered to also occur due to the heat treatment according to the present invention. It is just surprising that migration from the inside of the membrane base material to the surface of the membrane proceeds more rapidly than the oxidation and inactivation so that the antioxidant action of the blood treatment membrane remarkably increases.

In order to cause the inner surface of the membrane to have a normalized peak intensity of the lipophilic antioxidant of $1.4 \times 10^{-4}$ or more and cause the outer surface of the membrane to have a normalized peak intensity of the lipophilic antioxidant of $1.8 \times 10^{-4}$ or more using this method, the content of the lipophilic antioxidant must be 22 mg or more per gram of the blood treatment membrane. In addition, in order to cause the inner surface of the membrane to have a normalized peak intensity of the lipophilic antioxidant of $1.8 \times 10^{-4}$ or more and cause the outer surface of the membrane to have a normalized peak intensity of the lipophilic antioxidant of $2.4 \times 10^{-4}$ or more, the content of the lipophilic antioxidant must be 30 mg or more per gram of the blood treatment membrane.

The term "dry state" used in the present invention means that the membrane has at least a water content of not more than saturation water content, that is, the periphery of the membrane is not completely filled with water, and water does not drip. The water content is not particularly limited, but is preferably 0 to 100%, and more preferably 0 to 50%. If the water content is higher than 100%, the temperature of the blood treatment membrane does not increase due to evaporative latent heat of vaporization of water, even though heat is applied from the outside. Therefore, migration of the lipophilic antioxidant to the surface of the membrane is delayed until water evaporates.

The blood treatment membrane according to the present invention in a dry state may be heat-treated after completing the production of the blood treatment membrane, or may be heat-treated in a state that the blood treatment membranes are assembled into a module. It is preferable to continuously heat-treat the membrane immediately after drying in a drying step of a membrane production process from the viewpoint of productivity.

If the heat treatment temperature is low, migration of the lipophilic antioxidant to the surface does not sufficiently proceed. If the heat treatment temperature is high, the blood treatment membrane softens, or oxidation of the antioxidant proceeds. The heat treatment temperature is preferably 100 to 180° C., more preferably 110 to 180° C., and still more preferably 140 to 180° C. as exemplified the condition of the heat treatment. If the heat treatment time is short, migration of the lipophilic antioxidant to the surface does not sufficiently proceed. If the heat treatment time is long, oxidation of the antioxidant proceeds. The heat treatment time is preferably 0.1 to 360 minutes, and more preferably 0.5 to 300 minutes. It is preferable to reduce the heat treatment time when the heat treatment temperature is high, for example, the heat treatment time is preferably 0.1 to 1 minute when the heat treatment temperature is 140 to 180° C.

As described above, the polysulfone-based blood treatment membrane according to the present invention can be obtained by heat-treating the membrane that includes the polysulfone-based resin, the hydrophilic polymer, and the lipophilic antioxidant and contains the lipophilic antioxidant in an amount of 30 to 76 mg per gram of the membrane at 100 to 180° C. for 0.1 to 360 minutes in a dry state.

When heat-treating the membrane immediately after drying in a drying step of a membrane production process, the drying that removes water may not be clearly distinguished from the heat treatment that causes the lipophilic antioxidant to migrate to the surface of the membrane. The essence of the present invention is to heat-treat the blood treatment membrane, that is, to increase the temperature of the membrane base material. Therefore, when continuously heat-treating the blood treatment membrane immediately after drying, a drying step that removes water and is a period until the falling rate drying period may be distinguished from the heat treatment step after the constant-rate drying period that causes the lipophilic antioxidant to migrate to the surface of the membrane.

Figure 4:
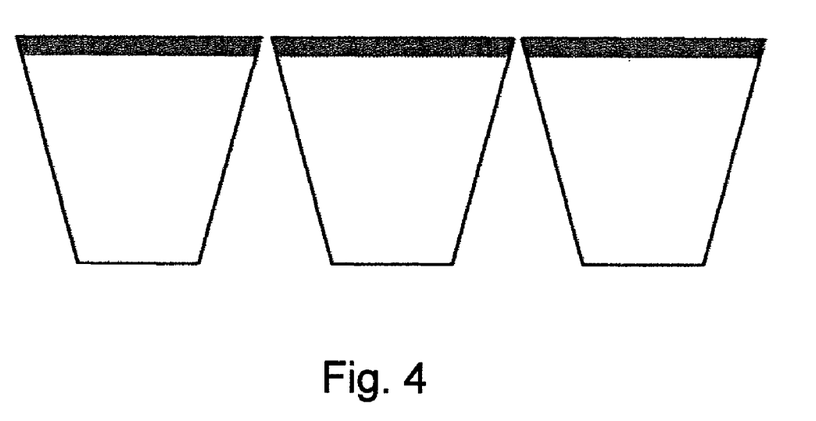
FIG. 4 is a schematic drawing showing polysulfone-based hollow treatment membranes of Comparative Examples 13 and 14. The lipophilic antioxidant is present on only the inner surface of the hollow fiber.
Figure 5:
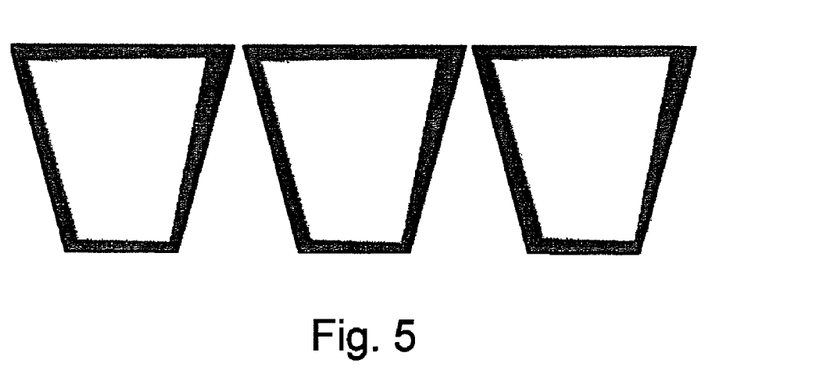
FIG. 5 is a schematic drawing showing a polysulfone-based hollow treatment membrane of Comparative Example 15. The lipophilic antioxidant is present on only the surface of the membrane, and is not present inside the polymer skeleton that forms the membrane base material.

As described above, the polysulfone-based blood treatment membrane according to the present invention includes the lipophilic antioxidant and exhibits excellent antioxidant properties, a capability of preventing entry of endotoxins through the outer surface of the membrane, and a practical strength, although these properties have been previously difficult to achieve simultaneously. Moreover, in the blood treatment membrane according to the present invention the lipophilic antioxidant is present in the entire membrane, this is effective to prevent elution of a low-molecular-weight substance that is undesirable for a human body and caused by oxidative decomposition of the polymer that forms the membrane during long-term storage of the blood treatment membrane. A polymer material used for a blood treatment membrane is confirmed to be fully safe. However, there may be risk that a defense mechanism of a living body may act when excessive elution occurs so that oxidative stress may occur. A coated-type membrane in which a lipophilic antioxidant is not included inside the membrane (see Patent Document 1, 2 and 3 and FIG. 4 or 5) exhibits insufficient resistance to oxidative decomposition. This problem is also improved.

EXAMPLES

The present invention is further described below by way of examples in which vitamin E was used as the lipophilic antioxidant. Note that the present invention is not limited to the following examples. The raw materials, reagents, and measuring methods used in the examples are described below.

[Raw Material and Reagent]
 1. PSf: "P-1700" manufactured by Solvay Advanced Polymers
 2. PVP: "K-90" manufactured by ISP
 3. Vitamin E (dl-α-tocopherol): manufactured by DSM Nutrition Japan K.K. (pharmacopeial preparation)
 4. α-Tocopherol acetate: manufactured by Wako Pure Chemical Industries, Ltd. (special grade)
 5. Pluronic F-68: polyethylene glycol-polypropylene glycol copolymer; manufactured by Adeka Corporation
 6. DMAc: manufactured by Kishida Chemical Co., Ltd. (special grade)
 7. DMSO: manufactured by Kishida Chemical Co., Ltd. (special grade)
 8. N,N-Dimethylformamide (hereinafter, abbreviate as DMF): manufactured by Kishida Chemical Co., Ltd. (special grade)
 9. 1-Methyl-2-pyrrolidone (hereinafter, abbreviate as NMP): manufactured by Tokyo Chemical Industry Co., Ltd. (special grade)
 10. Ferric chloride hexahydrate: manufactured by Wako Pure Chemical Industries, Ltd. (special grade)
 11. Ethanol: manufactured by Wako Pure Chemical Industries, Ltd. (special grade)
 12. 2,2'-Bipyridyl: manufactured by Wako Pure Chemical Industries, Ltd. (special grade)
 13. Water for Injection (pure water): manufactured by Otsuka Pharmaceutical Co., Ltd.
 14. Antioxidant assay kit: "PAO" manufactured by Nikken Seil Co., Ltd.

[Vitamin E Content in Entire Blood Treatment Membrane (Hereinafter, Abbreviate as "Bulk VE Content")]

The dried blood treatment membrane was dissolved in NMP (about 3 wt %) to prepare a measurement liquid. The vitamin E concentration of the measurement liquid was determined using a peak area corresponding to vitamin E measured by liquid chromatography (column: Inertsil C8-3 μm (4.6 (φ)×250 mm)+ODP-50 6E (4.6 (φ)×250 mm), eluent: NMP, flow rate: 0.5 ml/min, column temperature: 40° C., UV detector wavelength: 295 nm) and a calibration curve separately created using a standard solution having a known concentration. The vitamin E content (mg) per gram of the membrane (=bulk VE content (mg/g)) was calculated from the obtained vitamin E concentration and the dilution.

[Content of Vitamin E Present on Surface of Membrane (Hereinafter, Abbreviate as "Membrane Surface VE Content")]

Ferric chloride hexahydrate was dissolved in pure water to prepare a 0.3 w/v % aqueous solution. 1 g of the blood treatment membrane and 20 ml of the ferric chloride aqueous solution were placed in a glass bottle. After defoaming the mixture at 60 mmHg for 10 minutes, the mixture was incubated at 30° C. for four hours with shaking (vitamin E present on the surface of the membrane reduced iron (III) ions to produce iron (II)). 2.6 ml of the incubated aqueous solution, 0.7 ml of ethanol, and 0.7 ml of a 0.5 w/v % 2,2'-bipyridyl ethanol solution separately prepared were mixed, and the mixture was incubated at 30° C. for 30 minutes with shaking (iron (II) and bipyridyl formed a complex to give a color). The absorbance of the colored liquid at 520 nm was measured using a spectrophotometer. The weight (mg) of vitamin E present on the surface per 1 g of the blood treatment membrane (=membrane surface VE content (mg/g)) was determined using a calibration curve created by performing the incubation, color reaction, and absorbance measurement using a vitamin E ethanol solution having a known concentration instead of the blood treatment membrane in a same way.

[Vitamin E Normalized Peak Intensity on Outer Surface of Membrane]

The intensity of outer surface of the dried blood treatment membrane (hollow fiber) or the inner surface of the membrane exposed by incising the hollow fiber in the longitudinal direction was measured using a TOF-SIMS instrument ("TRIFTIII" manufactured by Physical Electronics, Inc.). The measurement was conducted under the following condition: primary ion $Ga^+$, an accelerating voltage of 15 kV, a current of 600 pA (DC), an analysis area of 200×200 µm, and an integration time of five minutes, and a negative ion (vitamin E: 163 (mass)) was detected using the detector. The measurement depth was 5 nm from the surface depending on the characteristics of the measuring instrument. The vitamin E normalized peak intensity was calculated by the following expression (5) using the obtained vitamin E peak ion intensity (IV), proton ion intensity IH and total ion intensity IT.

$$\text{Normalized peak intensity} = IV/(IT-IH) \quad (5)$$

[Toughness of Blood Treatment Membrane]

A single dried hollow fiber membrane (length 20 cm) was secured on a tensile tester (EZ Test series manufactured by Shimadzu Corporation) using a chuck in a room where the temperature was 20 to 25° C. and the humidity was 55 to 60 RH %, and was pulled at a tensile rate of 30 cm/min to measure the strength (gf) at break.

A value obtained by dividing the elongation at break of the hollow fiber membrane by the length (20 cm) of the hollow fiber membrane before the measurement, and multiplying the resulting value by 100 was determined to be the elongation (%), and the toughness was calculated by the following expression (6).

$$\text{Toughness(gf·\%)} = \text{strength at break(gf)} \times \text{elongation at break(\%)} \quad (6)$$

[Antioxidant Capability]

2 g of the blood treatment membrane was cut to a length of 2 to 3 mm, and primed using a physiological saline solution. After the addition of 2 ml of heparinized fresh human blood, the mixture was incubated at 37° C. for four hours with shaking. Blood collected from three persons was separately used for a single membrane (n=3 test). Plasma was then collected by centrifugation. The antioxidant capability (PAO) of the collected plasma was measured using a test kit for Potential Anti Oxidant "PAO" (Nikken Seil Co., Ltd.). A biological reaction occurs by causing blood to come in contact with the membrane, and the PAO value decreases. The decrease in PAO value is suppressed in the membrane having an antioxidant capability. Therefore, the blood treatment membrane may be determined to have a higher blood antioxidant capability as the PAO value increases. The resulting PAO value was compared with the PAO value obtained by causing blood to come in contact with a control membrane (Comparative Example 1) that did not contain the lipophilic antioxidant, and a significance test (t test) was conducted (one-sided 5%).

[Endotoxin Entry Rate (Hereinafter, Abbreviate as "ET Permeability")]

A fiber bundle consisting of 9984 blood treatment membranes was placed in a tubular housing (length: about 280 mm) having two nozzles (dialysate-side nozzles) on the opposite sides thereof. After embedding each end of the housing in a urethane resin, the cured urethane portion was cut so that the hollow fiber membranes were open on each end. Each end of the housing was provided with a header cap having a liquid inlet nozzle (or a liquid outlet nozzle) (blood-side nozzle) to assemble in the shape of a dialysis module, and the resulting product was secured so that the blood-side nozzles faced upward and downward.

Tap water adjusted to an endotoxin concentration of 97100 EU/L as a model liquid for infected dialysate was introduced through the lower side D nozzle at a flow rate of 500 ml/min using a pump, and discharged through the upper part B nozzle for 20 minutes by backfiltration from the dialysate side to the blood side. The filtrate after 20 minutes of discharge was then sampled to measure the endotoxin concentration. The ET permeability (%) was calculated to two places of decimals as a ratio with respect to the endotoxin concentration before filtration. The endotoxin concentration was measured by colorimetry method (time analysis) using an endotoxin measuring instrument ("Toxinometer ET-2000" manufactured by Wako Pure Chemical Industries, Ltd.) and an LAL exclusive reagent (manufactured by Wako Pure Chemical Industries, Ltd.).

[Evaluation of Air Permeability from Blood Treatment Membrane]

A fiber bundle consisting of 9984 blood treatment membranes was placed in a tubular housing (length: about 280 mm). After embedding each end of the housing in a urethane resin, the cured urethane portion was cut so that the hollow fiber membranes were open on each end. Each end of the housing was provided with a header cap having a liquid inlet (outlet) nozzle to assemble in the shape of a module, and the resulting product was secured so that the nozzles faced upward and downward. Water for injection was introduced through the lower nozzle using a pump at a flow rate of 100 ml/min, and discharged through the upper nozzle to replace air contained in the module with the water for injection. After replacement, 10 ml of air was then injected through the lower nozzle using a syringe while causing the water for injection to flow through the module. Air that was discharged through the upper nozzle together with the water for injection was collected. The air recovery rate was calculated from the ratio of the collection amount after 10 minutes to the injection amount. It means that low air recovery rate indicates low air permeability, and indicates that permeability may be adversely affected by air remaining in an area from the membrane thickness portion to the outer surface.

[Measurement of Surface PVP Concentration]

The surface PVP concentration of the hollow fiber membrane was determined by X-ray photoelectron spectroscopy (XPS). Specifically, a sample was prepared by placing several hollow fiber membranes on a double-sided adhesive tape for outer surface measurement or prepared by placing several hollow fiber membranes of which the inner surface was exposed by cutting the hollow fiber membrane in the longitudinal direction on a double-sided tape for inner surface measurement, and the surface element concentration was measured by a normal method. The surface nitrogen concentration (A) and the surface sulfur concentration (B) were calculated using an attached relative sensitivity coefficient from the obtained area intensities of the C1s, O1s, N1s, and S2p spectra, and the inner surface PVP concentration was calculated by the following expression (7).

$$\text{Inner surface PVP concentration} = \{A \times 111/(A \times 111 + B \times C)\} \times 100(\%) \quad (7)$$

Wherein, C is "formula weight/number of sulfur elements" of the PSf repeating unit (=442 when the PSf is shown by the formula (1)). 111 in the expression (7) is "formula weight/number of nitrogen elements" of the PSf repeating unit.

[Measurement of Outer Surface Contact Angle]

The advancing contact angle and the receding contact angle of the hollow fiber membrane that was sealed on each end using a heated knife were measured using a dynamic contact angle measuring device "DataPhysics DCAT11" (manufactured by DataPhysics Instruments GmbH) and attached software. The measurement conditions are given below. Immersion liquid: water for injection, water temperature: 25° C., immersion rate: 0.10 mm/sec, immersion depth: 10.00 mm, repetition number of measurements: six (data other than the first data was averaged)

[Long-Term Storage Stability Model Test]

The blood treatment membrane was assembled into a hemodialysis module as follows. Specifically, a fiber bundle consisting of 9984 blood treatment membranes was placed in a tubular housing (length: about 280 mm). After embedding each end of the housing in a urethane resin, the cured urethane portion was cut so that the hollow fiber membranes were open on each end. Each end of the housing was provided with a header cap having a liquid inlet (outlet) nozzle to assemble in the shape of a module. A 300 ppm sodium pyrosulfite aqueous solution was introduced into the module, and γ-rays (25 kGy) were applied in a state in which each nozzle was stoppered tightly. The resulting module was heat-treated in a temperature-controlled storage at 60° C. for three weeks, that is, acceleration test corresponding to long-term storage was conducted.

1.5 g of the blood treatment membranes removed by disassembling the module before and after heating were extracted with 150 ml of pure water (70° C.) for one hour. The UV spectrum (220 to 350 nm) of the extract was measured, and the maximum absorbance was taken as an alternative index of the amount of substance eluted from the blood treatment membranes.

Example 1

A membrane-forming raw spinning solution consisting of 17 parts by weight of the PSf, 4 parts by weight of PVP, 0.6 parts by weight of α-tocopherol, and 78.4 parts by weight of DMAc was prepared. A 41 wt % DMAC aqueous solution was used as a hollow-making inner solution. The membrane-forming raw spinning solution was extruded from a spinneret having a slit width of 50 μm. The temperature of the membrane-forming raw spinning solution during extrude was 60° C. The extruded membrane-forming raw spinning solution was immersed in a coagulation bath (90° C.) which contains water and is provided 50 cm below the spinneret through a hooded fall area, coagulated at 30 m/min, refined, and introduced into a dryer. After falling rate drying the coagulated product at 120° C. for two minutes, the product was heat-treated at 180° C. for 0.3 minutes. The hollow fiber membranes were then wound up to obtain a bundle consisting of 9984 hollow fiber membranes. The extrude amount of the membrane-forming raw spinning solution and the hollow-making inner solution was adjusted so that the thickness and inner diameter of the membrane after drying was adjusted to 45 μm and 185 μm, respectively (the thickness and the inner diameter were similarly adjusted in the following examples and comparative examples).

The resulting hollow fiber membrane bundle had a bulk VE content of 30 mg/g, a surface VE content of 4.0 mg/g, and a VE normalized peak intensity of $1.8 \times 10^{-4}$ (inner surface) and $2.4 \times 10^{-4}$ (outer surface). The average PAO value obtained by the human blood test was 1154 (human blood A: 1121, human blood B: 1260, and human blood C: 1082). The membrane had a toughness of 1265 gf·%. The ET permeability was 0.01%. The inner surface PVP content was 36%, and the outer surface PVP content was 47%. The outer surface had a receding contact angle of 15° and an advancing contact angle of 44°.

The obtained hollow fiber membrane bundle was assembled into a hemodialysis module, and subjected to the long-term storage stability model test. The UV absorbance of the eluate was 0.06 before heating and 0.06 after heating). The treatment conditions and the measured values are shown in Table 1 (hereinafter the same).

Example 2

A membrane-forming raw spinning solution consisting of 17 parts by weight of the PSf, 4 parts by weight of PVP, 2 parts by weight of α-tocopherol, and 77 parts by weight of DMAc was used. The membrane-forming raw spinning solution was coagulated, refined, dried, heat-treated, and wound in the same manner as in Example 1 to obtain a hollow fiber membrane bundle.

The resulting hollow fiber membrane bundle had a bulk VE content of 76 mg/g, a surface VE content of 20 mg/g, and a VE normalized peak intensity of $13 \times 10^{-4}$ (inner surface) and $22 \times 10^{-4}$ (outer surface). The average PAO value obtained by the human blood test was 2023 (human blood A: 2063, human blood B: 2155, and human blood C: 1850). The membrane had a toughness of 1125 gf·%. The ET permeability was 0.01%.

Example 3

A membrane-forming raw spinning solution prepared in the same manner as in Example 2 was coagulated, refined, and dried in the same manner as in Example 2. After heating the resulting product at 170° C. for one minute, the hollow fiber membranes were wound to obtain a hollow fiber membrane bundle consisting of 9984 hollow fiber membranes.

The resulting hollow fiber membrane bundle had a bulk VE content of 76 mg/g, a surface VE content of 25 mg/g, a VE normalized peak intensity of $4.3 \times 10^{-4}$ (inner surface) and $85 \times 10^{-4}$ (outer surface), and an air recovery rate of 97%. The average PAO value obtained by the human blood test was 2625 (human blood A: 2482, human blood B: 2829, and human blood C: 2564). The membrane had a toughness of 1125 gf·%. The ET permeability was 0.01%.

Comparative Example 1

A membrane-forming raw spinning solution consisting of 17 parts by weight of the PSf, 4 parts by weight of PVP, and 79 parts by weight of DMAc was used. The membrane-forming raw spinning solution was coagulated, refined, dried, heat-treated, and wound in the same manner as in Example 1 to obtain a hollow fiber membrane bundle.

The resulting hollow fiber membrane bundle had a bulk VE content of 0 mg/g, a VE normalized peak intensity of 0.0 (both inner surface and outer surface), and an air recovery rate of 99%. The average PAO value obtained by the human blood test was 841 (human blood A: 894, human blood B: 747, and human blood C: 881). The membrane had a toughness of 1265 gf·%. The ET permeability was 0.24%. The inner surface PVP content was 35%, and the outer surface PVP content was 47%. The outer surface had a receding contact angle of 14° and an advancing contact angle of 32°.

The hollow fiber membrane bundle was assembled into a hemodialysis module, and subjected to the long-term storage stability model test. The UV absorbance of the eluate was 0.06 before heating and 0.19 after heating.

Comparative Example 2

A membrane-forming raw spinning solution consisting of 15 parts by weight of the PSf, 9 parts by weight of PVP, 0.5 parts by weight of α-tocopherol, 30 parts by weight of DMAc, and 46 parts by weight of DMSO, and a hollow-making inner solution consisting of 30 wt % of DMAc, 30 wt % of DMSO, and 40 wt % of water, were used. The membrane-forming raw spinning solution was coagulated and refined in the same manner as in Example 1, and 9984 hollow fiber membranes were wound in a wet state.

The resulting hollow fiber membrane bundle was falling-rate-dried at 80° C. for 420 minutes, and heat-treated at 80° C. for 240 minutes. The resulting hollow fiber membrane bundle had a bulk VE content of 24 mg/g, a surface VE content of 0.4 mg/g, and a VE normalized peak intensity of $8.9 \times 10^{-5}$ (inner surface) and $8.8 \times 10^{-5}$ (outer surface). The average PAO value obtained by the human blood test was 850 (human blood A: 852, human blood B: 772, and human blood C: 926). The membrane had a toughness of 1131 gf·%. The ET permeability was 0.19%.

Comparative Example 3

A membrane-forming raw spinning solution including 17 parts by weight of the PSf, 4 parts by weight of PVP, 0.4 parts by weight of α-tocopherol, and 77 parts by weight of DMAc was used. The membrane-forming raw spinning solution was coagulated, refined, dried, heat-treated, and wound in the same manner as in Example 1 to obtain a hollow fiber membrane bundle.

The resulting hollow fiber membrane bundle had a bulk VE content of 20 mg/g, a surface VE content of 2.9 mg/g, and a VE normalized peak intensity of $1.0 \times 10^{-4}$ (inner surface) and $1.4 \times 10^{-4}$ (outer surface). The average PAO value obtained by the human blood test was 887 (human blood A: 938, human blood B: 853, and human blood C: 870). The membrane had a toughness of 1140 gf·%. The ET permeability was 0.15%.

Comparative Example 4

A membrane-forming raw spinning solution prepared in the same manner as in Example 2 was coagulated, refined, wound, dried, and heat-treated in the same manner as in Example 2 to obtain a hollow fiber membrane bundle.

The resulting hollow fiber membrane bundle had a bulk VE content of 76 mg/g, a surface VE content of 3.8 mg/g, and a VE normalized peak intensity of $1.5 \times 10^{-4}$ (inner surface) and $1.5 \times 10^{-4}$ (outer surface). The average PAO value obtained by the human blood test was 1075 (human blood A: 1101, human blood B: 1278, and human blood C: 846). The membrane had a toughness of 1125 gf·%. The ET permeability was 0.12%.

Comparative Example 5

A membrane-forming raw spinning solution consisting of 17 parts by weight of the PSf, 4 parts by weight of PVP, 2.1 parts by weight of α-tocopherol, and 76.9 parts by weight of DMAc was used. The membrane-forming raw spinning solution was coagulated, refined, dried, heat-treated, and wound in the same manner as in Example 1 to obtain a hollow fiber membrane bundle.

The resulting hollow fiber membrane bundle had a bulk VE content of 80 mg/g, a surface VE content of 8.8 mg/g, and a VE normalized peak intensity of $2.2 \times 10^{-4}$ (inner surface) and $4.2 \times 10^{-4}$ (outer surface). The membrane had a toughness of 950 gf·%. The ET permeability was 0.01%.

Comparative Example 6

A membrane-forming raw spinning solution was coagulated, refined, dried, and wound in the same manner as in Comparative Example 5, except for heat-treating the dried product at 180° C. for one minute, to obtain a hollow fiber membrane bundle.

The resulting hollow fiber membrane bundle had a bulk VE content of 80 mg/g, a surface VE content of 15 mg/g, and a VE normalized peak intensity of $8.4 \times 10^{-4}$ (inner surface) and $16 \times 10^{-4}$ (outer surface). The membrane had a toughness of 950 gf·%. The ET permeability was 0.01%.

TABLE 1

|  | Example 1 | Example 2 | Example 3 | Comparative Example 1 | Comparative Example 2 | Comparative Example 3 | Comparative Example 4 | Comparative Example 5 | Comparative Example 6 |
|---|---|---|---|---|---|---|---|---|---|
| Bulk VE content (mg/g) | 30 | 76 | 76 | 0.0 | 24 | 20 | 76 | 80 | 80 |
| Heating conditions |  |  |  |  |  |  |  |  |  |
| Temperature (° C.) | 180 | 180 | 170 | 180 | 80 | 180 | 80 | 180 | 180 |
| Time (min) | 0.3 | 0.3 | 1 | 0.5 | 240 | 0.5 | 420 | 0.3 | 1.0 |
| Surface VE content (mg/g) | 4.0 | 20 | 25 | 0.0 | 0.4 | 2.9 | 3.8 | 8.8 | 15 |
| Inner surface VE normalized peak intensity (—) $\times 10^{-4}$ | 1.8 | 13 | 4.3 | 0.0 | 0.89 | 1.0 | 1.5 | 2.2 | 8.4 |
| Outer surface VE normalized peak intensity (—) $\times 10^{-4}$ | 2.4 | 22 | 85 | 0.0 | 0.88 | 1.4 | 1.5 | 4.2 | 16 |
| PAO value | 1154 | 2023 | 2625 | 841 | 850 | 887 | 1075 | Not measured | Not measured |
| P value of PAO value[*1] | [*] 0.04 | [] 0.01 | [] 0.01 | Control — | [ ] 0.38 | [ ] 0.15 | [ ] 0.14 | Not measured | Not measured |
| ET permeability | 0.01 | 0.01 | 0.01 | 0.24 | 0.19 | 0.15 | 0.12 | 0.01 | 0.01 |
| Toughness (gf·%) | 1265 | 1125 | 1125 | 1265 | 1131 | 1140 | 1125 | 950 | 950 |
| Surface VE/bulk VE ratio | 0.13 | 0.26 | 0.33 | — | 0.02 | 0.15 | 0.05 | 0.11 | 0.19 |

[*1] No significant difference from Comparative Example 1 [ ]; significant difference from Comparative Example 1 [*] (risk factor: 5%); significant difference from Comparative Example 1 [**] (risk factor: 1%)

As is clear from the comparison between Examples 1 and 2 and Comparative Examples 1 and 2 shown in Table 1, in order to provide excellent antioxidant properties and a capability of preventing entry of endotoxins in comparison with the blood treatment membrane of Comparative Example 1 that did not contain vitamin E, the surface VE content must be 4.0 mg/g or more, and the VE normalized peak intensity on the outer surface of the membrane must be $2.4 \times 10^{-4}$ or more. Further, as is clear from the comparison between Example 1 and Comparative Example 3, the bulk VE content must be 30 mg/g or more in order to achieve a surface VE content of 4.0 mg/g or more. Furthermore, as is clear from the comparison between Example 2 with Comparative Examples 5 and 6, the bulk VE content must be 76 mg/g or less in order to achieve a toughness of 1000 gf·% or more.

Comparative Example 2 is an examination for confirming the membrane described in Example 2 of Patent Document 4 of a prior art. In this case, the membrane exhibited sufficient mechanical strength, but had an insufficient membrane surface VE content. Therefore, the membrane of Comparative Example 2 did not exhibit superior antioxidant properties as compared with the blood treatment membrane of Comparative Example 1 that did not contain vitamin E, and exhibited an insufficient capability of preventing entry of end endotoxins.

The ratio of the surface VE content to the bulk VE content is focused here as an index of the uneven distribution of the lipophilic antioxidant on the surface of the membrane. Any blood treatment membranes according to the present invention (Examples) had a surface VE/bulk VE ratio significantly higher than those of the blood treatment membranes of Comparative Examples 2 and 4 in which the heat treatment was not performed. This suggests that the lipophilic antioxidant is unevenly distributed on the surface of the blood treatment membrane according to the present invention. As a result of the special uneven distribution, the opposite effects that antioxidant properties can be sufficiently increased even though the bulk VE content can be reduced to such an extent that the mechanical strength of the membrane is not impaired, can be achieved simultaneously.

Comparative Example 7

A membrane-forming raw spinning solution consisting of 17 parts by weight of the PSf, 4 parts by weight of PVP, 1.5 parts by weight of α-tocopherol, and 77.5 parts by weight of DMAc was used. The membrane-forming raw spinning solution was coagulated, refined, and wound in the same manner as in Comparative Example 2 to obtain a hollow fiber membrane bundle in a wet state. The hollow fiber membrane bundle was then dried at 80° C. for seven hours.

The resulting hollow fiber membrane bundle had a bulk VE content of 59 mg/g, a surface VE content of 2.2 mg/g, and a VE normalized peak intensity of $0.8 \times 10^{-4}$ (inner surface) and $0.8 \times 10^{-4}$ (outer surface). The ET permeability was 0.19%. The treatment conditions and the measured values are shown in Table 2 (hereinafter the same).

Comparative Example 8

The hollow fiber membrane bundle of Comparative Example 7 was heat-treated at 90° C. for 360 minutes.

The resulting hollow fiber membrane bundle had a bulk VE content of 59 mg/g, a surface VE content of 2.7 mg/g, and a VE normalized peak intensity of $1.0 \times 10^{-4}$ (inner surface) and $1.0 \times 10^{-4}$ (outer surface). The ET permeability was 0.19%.

Example 4

The hollow fiber membrane bundle of Comparative Example 7 was heat-treated at 100° C. for 360 minutes.

The resulting hollow fiber membrane bundle had a bulk VE content of 59 mg/g, a surface VE content of 4.4 mg/g, and a VE normalized peak intensity of $2.2 \times 10^{-4}$ (inner surface) and $2.4 \times 10^{-4}$ (outer surface). The ET permeability was 0.01%.

Example 5

The hollow fiber membrane bundle of Comparative Example 7 was heat-treated at 110° C. for 360 minutes.

The resulting hollow fiber membrane bundle had a bulk VE content of 59 mg/g, a surface VE content of 13 mg/g, and a VE normalized peak intensity of $6.8 \times 10^{-4}$ (inner surface) and $30 \times 10^{-4}$ (outer surface). The ET permeability was 0.01%.

Example 6

The hollow fiber membrane bundle of Comparative Example 7 was heat-treated at 180° C. for 0.6 min The resulting hollow fiber membrane bundle had a bulk VE content of 59 mg/g, a surface VE content of 7.5 mg/g, and a VE normalized peak intensity of $3.5 \times 10^{-4}$ (inner surface) and $16 \times 10^{-4}$ (outer surface). The ET permeability was 0.01%.

Comparative Example 9

The hollow fiber membrane bundle of Comparative Example 7 was heat-treated at 190° C. for 0.1 minutes, and the bundle was attempted to be wound. The hollow fiber membrane bundle however could not be wound due to softening.

Comparative Example 10

A membrane-forming raw spinning solution consisting of 17 parts by weight of the PSf, 4 parts by weight of PVP, 1 part by weight of α-tocopherol, and 78 parts by weight of DMAc was used. The membrane-forming raw spinning solution was coagulated and refined in the same manner as in Comparative Example 2 to obtain hollow fiber membranes. 100 hollow fiber membranes were wound to obtain a hollow fiber membrane bundle in a wet state. The hollow fiber membrane bundle in a wet state was then dried at 80° C. for three hours.

The resulting hollow fiber membrane bundle had a bulk VE content of 40 mg/g, a surface VE content of 0.5 mg/g, a VE normalized peak intensity of $0.91 \times 10^{-4}$ (inner surface) and $0.96 \times 10^{-4}$ (outer surface), and an ET permeability of 0.20%.

Example 7

The hollow fiber membrane bundle of Comparative Example 10 was heat-treated at 140° C. for one minute.

The resulting hollow fiber membrane bundle had a bulk VE content of 40 mg/g, a surface VE content of 4.0 mg/g, a VE normalized peak intensity of $1.8 \times 10^{-4}$ (inner surface) and $2.3 \times 10^{-4}$ (outer surface), and an ET permeability of 0.01%.

Example 8

The hollow fiber membrane bundle of Comparative Example 10 was heat-treated at 180° C. for 0.1 minutes.

The resulting hollow fiber membrane bundle had a bulk VE content of 40 mg/g, a surface VE content of 7.9 mg/g, a VE normalized peak intensity of $2.3 \times 10^{-4}$ (inner surface) and $3.2 \times 10^{-4}$ (outer surface), and an ET permeability of 0.01%.

Comparative Example 11

The hollow fiber membrane bundle of Comparative Example 10 was heat-treated at 190° C. for 0.1 minutes. As a result, the hollow fibers softened and adhered. Therefore, the subsequent evaluations were impossible, and a module could not be produced.

TABLE 2

Heat-treating conditions and surface VE content (membrane with a bulk VE content of 59 mg/g was heat-treated)

|  | Comparative Example 7 | Comparative Example 8 | Example 4 | Example 5 | Example 6 | Comparative Example 9 |
|---|---|---|---|---|---|---|
| Heating conditions |  |  |  |  |  |  |
| Temperature (° C.) | Not performed | 90 | 100 | 110 | 180 | 190 |
| Time (min) | performed | 360 | 360 | 360 | 0.6 | 0.1 |
| Surface VE content (mg/g) | 2.2 | 2.7 | 4.4 | 13 | 7.5 | *2 |
| Inner surface VE normalized peak intensity (—) ×$10^{-4}$ | 0.8 | 1.0 | 2.2 | 6.8 | 3.5 | *2 |
| Outer surface VE normalized peak intensity (—) ×$10^{-4}$ | 0.8 | 1.0 | 2.4 | 30 | 16 | *2 |
| ET permeability (%) | 0.19 | 0.19 | 0.01 | 0.01 | 0.01 | *2 |

*2 The blood treatment membrane softened (could not be produced)

TABLE 3

Heat-treating conditions and surface VE content (membrane with a bulk VE content of 40 mg/g was heat-treated)

|  | Comparative Example 10 | Example 7 | Example 8 | Comparative Example 11 |
|---|---|---|---|---|
| Heating conditions | Not performed | 140 | 180 | 190 |
| Temperature (° C.) |  |  |  |  |
| Time (min) |  | 1.0 | 0.1 | 0.1 |
| Surface VE content (mg/g) | 0.5 | 4.0 | 7.9 | *3 |
| Inner surface VE normalized peak intensity (—) ×$10^{-4}$ | 0.91 | 1.8 | 2.3 | *3 |
| Outer surface VE normalized peak intensity (—) ×$10^{-4}$ | 0.96 | 2.3 | 3.2 | *3 |
| ET permeability (%) | 0.20 | 0.01 | 0.01 | *3 |

*3 The blood treatment membrane softened (could not be produced)

As is clear from the comparison between Example 4 and Comparative Example 6 shown in Table 2, a temperature of 100° C. or more is necessary for sufficient migration of vitamin E to the surface of the membrane. As is clear from the comparison between Example 6 and Comparative Example 9 shown in Table 2 and the comparison between Example 8 and Comparative Example 11 shown in Table 3, the heating temperature must be 180° C. or less even at a minimum heating time of 0.1 minutes in order to stably produce the blood treatment membrane.

Comparative Example 12

The hollow fiber membrane bundle of Comparative Example 6 was heat-treated at 110° C. for 1080 minutes.

The resulting hollow fiber membrane bundle had a bulk VE content of 80 mg/g, a surface VE content of 24 mg/g, a VE normalized peak intensity of 6.2×$10^{-3}$ (inner surface), and an air recovery rate of 79%. The membrane had a toughness of 950 gf·%.

TABLE 4

Surface VE content and air removability

|  | Example 3 | Comparative Example 12 |
|---|---|---|
| Bulk VE content (mg/g) | 76 | 80 |
| Inner surface VE normalized peak intensity (—) | 4.3 × $10^{-3}$ | 6.2 × $10^{-3}$ |
| Air recovery rate (%) | 97 | 79 |

As is clear from the comparison between Example 3 and Comparative Example 12 shown in Table 4, the air recovery rate significantly decreases when the inner surface VE normalized peak intensity exceeds 4.3×$10^{-3}$.

TABLE 5

Surface PVP content and outer surface contact angle

|  | Example 1 | Comparative Example 1 |
|---|---|---|
| Outer surface PVP content (%) | 47 | 47 |
| Outer surface VE normalized peak intensity (—) | 2.4 × $10^{-4}$ | 0 |
| Outer surface receding contact angle (°) | 15 | 14 |
| Outer surface advancing contact angle (°) | 44 | 32 |

As shown in Table 5, although the blood treatment membrane of Example 1 and the blood treatment membrane of Comparative Example 1 had almost equal outer surface receding contact angles, the advancing contact angle of the blood treatment membrane of Example 1 was higher than that of the blood treatment membrane of Comparative Example 1. Specifically, the membrane of Example 1 exhibited hydrophilicity equal to that of the membrane that did not contain vitamin E due to the PVP chain even though vitamin E was present on the outer surface of the membrane of Example 1. This means that most of the PVP present on the outer surface of the membrane of Example 1 contributed to hydrophilicity without impairing the performance. Since the membrane of Example 1 had an advancing contact angle higher than that of the membrane of Comparative Example 1, the hydrophobic surface became predominant over the PVP chain in the membrane of Example 1 in a hydrophobic atmosphere. This phenomenon occurred due to the VE layer precipitated on the outer surface at a high rate.

Therefore, the blood treatment membrane according to the present invention such as that of Example 1 has a very low endotoxin permeability even if a very high-concentration endotoxin solution is applied. The fact that the endotoxin permeability was not almost recognized even in a severe test using such a high-concentration endotoxin solution suggests that the blood treatment membrane according to the present invention has a number of endotoxin adsorption sites and the sites are stable.

Comparative Example 13

A membrane-forming raw spinning solution consisting of 19 parts by weight of the PSf, 9 parts by weight of PVP, and 72 parts by weight of DMF, and a hollow-making inner solution prepared by adding 0.1 parts by weight of α-tocopherol acetate and 0.1 parts by weight of Pluronic F-68 to a mixture of 60 parts by weight of DMF and 40 parts by weight of water, were used. The membrane-forming raw spinning solution was coagulated in the same manner as in Example 1, and showered with hot water (60° C.) for one hour at 1 l/min. 9984 hollow fiber membranes were wound in a wet state. The hollow fiber membranes were then washed with hot water (110° C.) for one hour.

The resulting hollow fiber membrane bundle had a VE normalized peak intensity of $2.8 \times 10^{-4}$ (inner surface) and 0.0 (outer surface).

The obtained hollow fiber membrane bundle was assembled into a hemodialysis module, and subjected to the long-term storage stability model test. The UV absorbance of the eluate was 0.06 before heating and 0.17 after heating, and the ET permeability was 0.17%.

Comparative Example 14

A membrane-forming raw spinning solution (60° C.) consisting of 18.0 parts by weight of the PSf, 4.3 parts by weight of PVP, and 77.7 parts by weight of DMAc was extruded from a double-ring spinneret together with a hollow-making inner solution consisting of 30 parts by weight of DMAc and 70 parts by weight of water, caused to pass through an air gap of 0.96 m, and immersed in a coagulation bath (water, 75° C.). 9984 hollow fiber membranes were wound at 80 m/min. The passage from the spinneret to the coagulation bath was enclosed by a cylindrical tube. The humidity and the temperature inside the tube were respectively controlled to 54.5 and 51° C. while causing nitrogen gas containing steam to flow through the cylinder. The wound fiber bundle was cut, and was washed for two hours by showering hot water at 80° C. from the upper cut section of the bundle to remove the residual solvent from the membrane. The membrane was then dried to obtain a dry membrane having a water content of less than 1%.

The resulting hollow fiber membrane bundle was assembled into a hemodialysis module. A coating solution prepared by dissolving α-tocopherol (1 wt %) in a 57 wt % isopropanol aqueous solution was introduced into the hollow portion of the hollow fiber membrane from the blood introduction nozzle of the hemodialysis module for 52 seconds. The remaining solution was removed by flushing with air, and dry air (24° C.) was passed through the membrane for 30 minutes to remove the solvent by drying.

The hollow fiber membrane obtained by disassembling the hemodialysis module had a VE normalized peak intensity of $15 \times 10^{-4}$ (inner surface) and $0.8 \times 10^{-4}$ (outer surface).

The hemodialysis module was subjected to the long-term storage stability model test. The UV absorbance of the eluate was 0.07 before heating and 0.15 after heating, and the ET permeability was 0.16%.

Comparative Example 15

A membrane-forming raw spinning solution (60° C.) consisting of 15.0 parts by weight of the PSf, 9.0 parts by weight of PVP, 45.0 parts by weight of DMSO, 35.0 parts by weight of DMAc, and 1.0 parts by weight of water, and a hollow-making inner solution consisting of 30 parts by weight of DMSO, 30 parts by weight of DMA, and 40 parts by weight of water were used. The membrane-forming raw spinning solution was coagulated and refined in the same manner as in Example 1, and 9984 hollow fiber membranes were wound in a wet state.

The resulting hollow fiber membranes were dried at 80° C. for 420 minutes. The dry hollow fiber membranes were passed through a 10% α-tocopherol in hexane solution, and dried at 40° C. for 60 minutes to remove the solvent.

The resulting hollow fiber membrane bundle had a bulk VE content of 0.8 mg/g, a surface VE content of 0.8 mg/g, and a VE normalized peak intensity of $0.9 \times 10^{-4}$ (inner surface) and $0.9 \times 10^{-4}$ (outer surface).

The hollow fiber membrane bundle was assembled into a hemodialysis module, and subjected to the long-term storage stability model test. The UV absorbance of the eluate was 0.06 before heating and 0.13 after heating.

TABLE 6

| | Long-term storage stability (model test) | | | | |
| --- | --- | --- | --- | --- | --- |
| | Example 1 | Comparative Example 1 | Comparative Example 13 | Comparative Example 14 | Comparative Example 15 |
| Outer surface VE normalized peak intensity (—) | $2.4 \times 10^{-4}$ | 0 | 0 | $0.8 \times 10^{-4}$ | $0.9 \times 10^{-4}$ |
| UV absorbance of eluate (before heating) | 0.07 | 0.06 | 0.06 | 0.07 | 0.06 |
| UV absorbance of eluate (after heating) | 0.06 | 0.19 | 0.17 | 0.15 | 0.13 |

Comparative Example 13 corresponds to Example 2 of Patent Document 5, Comparative Example 14 corresponds to Example 3 of Patent Document 2, and Comparative Example 15 corresponds to Example 3 of Patent Document 4. As shown in Table 6, the elution amount of the blood treatment membrane according to the present invention was within the range of the dialysis-type artificial kidney device approval standard (Jun. 20, 1983, Yakuhatsu Notification No. 494; Notification by the Director-General of the Pharmaceutical Affairs Bureau, Ministry of Health and Welfare), that is, the absorbance was within 0.1 or less even after heating at 60° C. for three weeks that corresponds to long-term storage. On the other hand, the membrane of Comparative Example 1 that did not contain the lipophilic antioxidant, the membranes of Comparative Examples 13 and 14 in which the lipophilic antioxidant was not present on the outer surface and in the porous area, and the membrane of Comparative Example 15 in which the membrane base material did not contain the lipophilic antioxidant had an elution amount exceeding the standard to a large extent. The above results suggest that the blood treatment membrane according to the present invention exhibits excellent long-term storage stability.

Further, in Comparative Example 14, the step of securing the lipophilic antioxidant was added between the step of assembling the hemodialysis module and the wetting step. The step of securing the lipophilic antioxidant required about 30 minutes, which is three to six times the time generally required for the wetting step after the assembling step. Therefore, excessive decrease of productivity cannot be avoidable with respect to a product that does not contain an antioxidant, even if installation cost for the additional step is disregarded. Moreover, the coating solution significantly increases the running cost inevitably even if the solvent of the used coating solution is purified for reuse or the coating solution is disposed after using several times. On the other hand, the blood treatment membrane according to the present invention can be produced using the same facilities and the same production time as a conventional product that does not contain an antioxidant. Therefore, high productivity is clearly exhibited as compared with related art (Comparative Example 14).

In Comparative Example 15, an additional step was provided when producing the membrane although the step of assembling the hemodialysis module was performed in a same manner as known facilities and method. The man-hour required for these additional step and use of the solvent that is not used for a conventional blood treatment membrane or the blood treatment membrane according to the present invention significantly and inevitably increases the running cost as well as the coating method employed in Comparative Example 14. Note that Example 3 of Patent Document 4 does not specifically describe whether the blood treatment membrane bundle is coated with the lipophilic antioxidant solution in a state of cut bundle or the blood treatment membrane is coated with the lipophilic antioxidant solution during travel without cutting the blood treatment membrane. According to the experiment conducted by the present inventors, the coating solution did not reach the inside of the hollow by the latter method. Therefore, the blood treatment membrane was coated with the lipophilic antioxidant solution in Comparative Example 15 in a state of bundle.

INDUSTRIAL APPLICABILITY

The blood treatment membrane according to the present invention exhibits an excellent antioxidant action when caused to come in contact with blood, exhibits excellent long-term storage stability, rarely allows endotoxins to enter the treatment liquid, has a practical strength that prevents sudden accidents such as breakage of the membrane during production or use, and ensures high productivity. Therefore, the blood treatment membrane according to the present invention can be effectively and safely used for extracorporeal circulation treatment of blood such as hemodialysis.

The invention claimed is:

1. A polysulfone-based blood treatment membrane that is a permselective membrane comprising a polysulfone-based resin, a hydrophilic polymer and a lipophilic antioxidant, in which the membrane contains the lipophilic antioxidant in an amount of 30 to 76 mg per gram of the membrane, and the total amount of the lipophilic antioxidant present on the surface of the membrane is 4 to 25 mg per gram of the membrane, wherein the membrane is in the form of hollow fibers having inner and outer surfaces, the membrane having a skin layer on the inner surface of the hollow fiber and a porous structure between the skin layer and the outer surface.

2. The polysulfone-based blood treatment membrane according to claim 1, wherein the membrane has TOF-SIMS normalized peak intensities, that is an index indicating the concentration of the lipophilic antioxidant on the surface of the membrane, of $1.4 \times 10^{-4}$ or more for the inner surface of the membrane, and of $1.8 \times 10^{-4}$ or more for the outer surface of the membrane.

3. The polysulfone-based blood treatment membrane according to claim 1, wherein the lipophilic antioxidant is a lipophilic vitamin.

4. A polysulfone-based permselective membrane comprising a polysulfone-based resin, a hydrophilic polymer, and a lipophilic antioxidant, and produced using a membrane-forming raw spinning solution including the polysulfone-based resin, the hydrophilic polymer, the lipophilic antioxidant, and a solvent, in which the membrane is produced by obtaining a membrane intermediate that contains the lipophilic antioxidant in an amount of 30 to 76 mg per gram of the membrane intermediate, and then heat-treating the membrane intermediate at 100 to 180° C. for 0.1 to 360 minutes in a dry state with a water content equal to or less than saturation water content, so that the membrane contains the lipophilic antioxidant in an amount of 30 to 76 mg per gram of the membrane, and the total amount of the lipophilic antioxidant present on the surface of the membrane is 4 to 25 mg per gram of the membrane.

* * * * *

UNITED STATES PATENT AND TRADEMARK OFFICE
CERTIFICATE OF CORRECTION

PATENT NO. : 8,220,642 B2
APPLICATION NO. : 12/601543
DATED : July 17, 2012
INVENTOR(S) : J. Satoh et al.

Page 1 of 1

It is certified that error appears in the above-identified patent and that said Letters Patent is hereby corrected as shown below:

On Cover Page (57) Abstract, line 27 of the printed patent, please delete "Another polysulfone-based blood treatment membrane contains a lipophilic antioxidant in an amount of 30 to 76 mg per gram of the membrane, wherein the inner surface of the membrane has a TOF-SIMS normalized peak intensity of the lipohilic antioxidant of 1.8 times.10.sup.-4 or more, and the outer surface of the membrane has a TOF-SIMS normalized peak intensity of the lipophilic antioxidant of 2.4.times.10.sup.-4 or more. A method of producing a polysulfone-based blood treatment membrane that includes a polysulfone-based resin, a hydrophilic polymer, and a lipophilic antioxidant included producing a membrane intermediate that contains the lipophilic antioxidant in an amount of 30 to 76 mg per gram of the membrane intermediate, and heating the membrane intermediate at 100 to 180.degree. C. for 0.1 to 360 minutes in a dry state."

Signed and Sealed this
Nineteenth Day of March, 2013

Teresa Stanek Rea
*Acting Director of the United States Patent and Trademark Office*